United States Patent [19]

Nielsen

[11] Patent Number: 4,738,709
[45] Date of Patent: * Apr. 19, 1988

[54] HERBICIDALLY ACTIVE SUBSTITUTED BENZISOXAZOLES

[75] Inventor: Donald R. Nielsen, Wadsworth, Ohio

[73] Assignee: PPG Industries, Inc., Pittsburgh, Pa.

[*] Notice: The portion of the term of this patent subsequent to Feb. 18, 2003 has been disclaimed.

[21] Appl. No.: 800,947

[22] Filed: Nov. 26, 1985

Related U.S. Application Data

[63] Continuation-in-part of Ser. No. 690,291, Jan. 10, 1985, abandoned.

[51] Int. Cl.$^4$ ............... C07D 261/20; A01N 31/08
[52] U.S. Cl. ............................. 71/94; 71/88;
544/354; 546/153; 546/270; 548/112; 548/159;
548/221; 548/241; 548/243; 548/207
[58] Field of Search ............... 71/88, 94; 546/270;
548/112, 241, 243

[56] References Cited

U.S. PATENT DOCUMENTS

| 4,344,789 | 8/1982 | Krass | 71/123 |
| 4,375,981 | 3/1983 | Krass | 71/121 |
| 4,472,425 | 9/1984 | Sandmeier | 548/240 |
| 4,571,255 | 2/1986 | Nielsen | 548/241 |

FOREIGN PATENT DOCUMENTS 0056119 7/1982 European Pat. Off. ............. 71/121

Primary Examiner—Donald G. Daus
Assistant Examiner—B. Cassatt
Attorney, Agent, or Firm—Edward J. Whitfield

[57] ABSTRACT

This invention relates to herbicidally active substituted benzisoxazole (or benzisothiazole) compounds and to the use of such compounds to control the growth of noxious plants, i.e., weeds.

5 Claims, No Drawings

HERBICIDALLY ACTIVE SUBSTITUTED BENZISOXAZOLES

CROSS-REFERENCE TO RELATED APPLICATIONS

This application is a continuation-in-part of copending U.S. application Ser. No. 690,291 filed Jan. 10, 1985, now abandoned.

FIELD OF THE INVENTION

This invention relates to herbicidally active substituted benzisoxazole (or benzisothiazole) compounds and to the use of such compounds to control the growth of noxious plants, i.e., weeds.

DESCRIPTION OF THE INVENTION

This invention provides herbicidally active substituted benzisoxazole (or benzisothiazole) compounds represented by the Formula

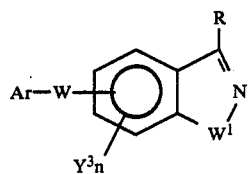

wherein Ar is

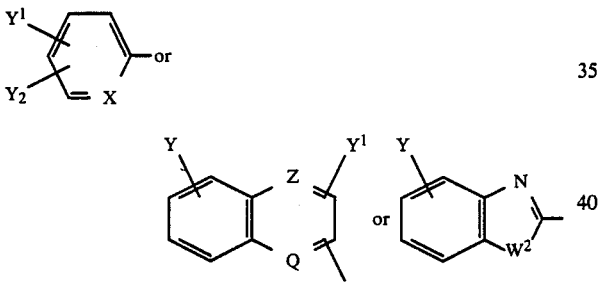

wherein:
W is oxygen, $S(O)_x$ or $NR^9$ wherein x is 0, 1 or 2 and $R^9$ is hydrogen or $C_1$ to $C_4$ alkyl;
$W^1$ and $W^2$ are independently oxygen or $S(O)_x$;
X is CY, N, $N^\oplus-O^\ominus$ or $N^\oplus-CH_3$;
Q is N or $N^\oplus-O^\ominus$;
Z is CH or N;
Y is hydrogen, halogen, cyano, nitro or lower haloalkyl;
$Y^1$ and $Y^2$ are independently hydrogen, halogen, nitro, cyano or lower alkyl, haloalkyl, alkoxy, alkoxyalkyl or alkyl sulfonyl;
$Y^3$ is halogen, cyano, nitro or lower haloalkyl and n is 0, 1, 2 or 3;
R is

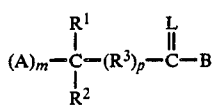

wherein A is oxygen, $S(O)_x$ or $NR^9$ and m is 0 or 1;
$R^1$ is hydrogen, halogen, nitro, cyano, $C_1$ to $C_4$ alkyl, haloalkyl, cycloalkyl, alkoxy or substituted alkoxy, alkoxyalkyl, carboxy, carboalkoxy, Ar, Ar-W, $Ar-R^4$ or $Ar-R^4-W$ wherein $R^4$ is $C_1$ to $C_4$ alkyl;
$R^2$ is hydrogen, halogen or $C_1$ to $C_4$ alkyl;
$R^3$ is up to $C_3$ alkylene, alkenyl or alkynyl which may be mono or disubstituted by a member or members selected from $R^1$;
p is 0 or 1;
B is hydrogen, $C_1$ to $C_6$ alkyl or haloalkyl, dialkylphosphonyl, $-OR^5$, $-SR^5$ or $-NR^6R^7$ wherein:
$R^5$ is hydrogen, alkali metal, ammonium or substituted ammonium, $C_1$ to $C_6$ alkyl, haloalkyl, oxoalkyl, hydroxyalkyl, thioalkyl, alkoxyalkyl, cycloalkyl, alkylene—$S(O)_x$—alkyl, alkenyl or alkynyl, alkoxycarbonyl alkyl including amides and salts thereof, trialkylammonium alkyl, or dialkylphosphonyl alkyl, Ar or $Ar-R^8$ wherein $R^8$ is $C_1$ to $C_4$ alkyl or $R^5$ is a 5 to 6 membered heterocyclic ring containing up to 3 hetero atoms;
$R^6$ and $R^7$ are independently hydrogen, $C_1$ to $C_6$ alkyl, alkoxy, alkoxyalkyl, alkylaminoalkyl, alkylsulfonyl, dialkylphosphonyl alkyl, alkylene—$S(O)_x$—alkyl, alkenyl or alkynyl or $R^6$ and $R^7$ may combine to form a 5 to 6 membered heterocyclic ring containing up to 3 hereto atoms; and
L is oxygen or $S(O)_x$ when B is $-OR^5$, $-SR^5$ or $-NR^6R^7$; but when B is hydrogen, alkyl or alkoxy L may also be dialkoxy or dioxyalkylene.

Although any herbicidally active compound within the scope of Formula I is contemplated by this invention, some preferred compounds are those represented by Formula II:

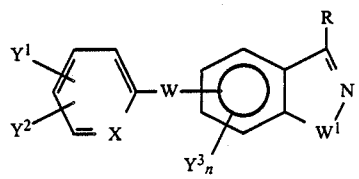

wherein X, $Y^1$, $Y^2$, $Y^3$, W, $W^1$, R and n are as previously defined.

Most preferred compounds are those Formula II compounds wherein $Y^1$ is a 2-halogen, e.g., chlorine or fluorine; $Y^2$ is a 4-lower haloalkyl, e.g., trifluoromethyl; X is CY wherein Y is hydrogen or halogen, e.g., chlorine or fluorine, W and $W^1$ are oxygen, n is 0 and R is

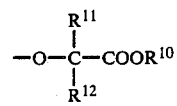

wherein $R^{11}$ is hydrogen or $C_1$ to $C_4$ alkyl; $R^{12}$ is hydrogen; and $R^{10}$ is $C_1$ to $C_4$ alkyl.

Also preferred is the 5-(aryloxy)-benzisoxazole isomer. Of course, the stereo isomers of the Formula I compounds are within the scope of this invention and in this regard certain of the stereo isomers, for example, the stereo isomers prepared from the R-isomers of alkyl-2-haloalkanoates have been observed to be particularly herbicidally active.

The compounds of the invention may be readily synthesized using methods known to the art. For example, certain of the Formula I compounds, i.e., those wherein A is oxygen, m is 1 and $W^1$ is oxygen, may be prepared by reacting a suitably substituted o-hydroxy benzoic acid ester of the Formula III:

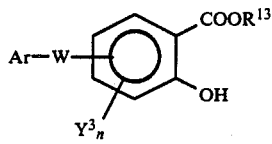

wherein Ar, W and $Y^3{}_n$ are as previously defined and $R^{13}$ is lower alkyl, e.g., methyl, with hydroxylamine hydrochloride in the presence of base to form the corresponding benzohydroxamic acid according to the method described, for example, by H. Boshagen in Chem. Ber. 100, 954 (1967).

The hydroxamic acid is then converted to the 3-hydroxy benzisoxazole of the Formula IV:

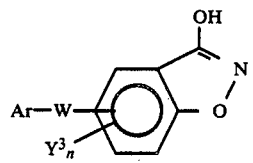

by a first reaction with thionyl chloride and then by reaction with triethylamine as described in Chem. Ber., supra.

The Formula IV compound is then reacted with a suitably substituted halogenated compound of the Formula V.

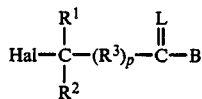

wherein Hal is halogen, e.g., bromine or chlorine, and $R^1$, $R^2$, $R^3$, p, L and B are as previously defined to form a compound of the invention.

The preparation of certain specific compounds of the invention are illustrated by the following Examples:

EXAMPLE I

Preparation of:
5-(2-chloro-4-trifluoromethylphenoxy)-3-hydroxybenzisoxazol-O-(acetic acid, methyl ester)

A mixture of 46.27 grams (0.30 mole) of 2,5-dihydroxybenzoic acid, 79.51 grams (0.40 mole) of 3-chloro-4-fluoro benzotrifluoride, 124.45 grams (0.90 mole) of potassium carbonate and 500 milliliters of dimethylsulfoxide was heated, with stirring, at 100° C. for 26 hours. The reaction mixture was then cooled, poured into 1.25 liters of water and extracted three times with methylene chloride. After phase separation, the aqueous phase was acidified with concentrated hydrochloric acid and extracted with methylene chloride. Evaporation of solvent afforded 126.7 grams of 5-(2-chloro-4-trifluoromethylphenoxy)-2-hydroxybenzoic acid. A solution of 91.9 grams of this hydroxybenzoic acid in methanol was esterified in the presence of anhydrous hydrochloric acid affording 95.1 grams of methyl 5-(2-chloro-4-trifluoromethylphenoxy)-2-hydroxybenzoate. Using the procedure described by H. Boshagen, Chem. Ber. 100, 954 (1967), 69.51 grams (0.20 mole) of the ester, 20.85 grams (0.30 mole) of hydroxylamine hydrochloride and 28.29 grams (0.71 mole) of sodium hydroxide were reacted in aqueous dioxane. The crude reaction product was partially evaporated then acidified and extracted with methylene chloride. After evaporation of solvent, the residue was slurried with aqueous methanol and suction filtered affording 44.47 grams of 5-(2-chloro-4-trifluoromethylphenoxy)-2-hydroxybenzohydroxamic acid melting at 188°-191° C. Again using the procedure described by H. Boshagen, supra, 13.91 grams (0.04 mole) of the hydroxamic acid and 10.55 grams (0.089 mole) of thionyl chloride in 40 milliliters of tetrahydrofuran were reacted in the first step and 12.17 gram of triethylamine in 40 milliliters of dioxane were used in the second step. The crude product (8.86 grams) was slurried in methylene chloride and suction filtered affording 6.57 grams of 5-(2-chloro-4-trifluoromethylphenoxy)-3-hydroxybenzisoxazole melting at 167°-170° C. To a solution of 1.98 grams (0.006 mole) of the 3-hydroxybenzisoxazole and 2.43 grams (0.016 mole) of methyl bromoacetate in 20 milliliters of acetonitrile were added 1.80 grams (0.013 mole) of potassium carbonate. After stirring at room temperature for 22 hours, solvent was evaporated at reduced pressure, water and methylene chloride were added to the residue, the phases were separated and the organic layer was washed twice with water. Evaporation of solvent at reduced pressure afforded 2.61 grams of oil which was purified by column chromatography and identified by MS and NMR analysis as the desired product, 5-(2-chloro-4-trifluoromethylphenoxy)-3-hydroxybenzisoxazol-O-(acetic acid, methyl ester).

EXAMPLE II

Preparation of:
5-(2-chloro-4-trifluoromethylphenoxy)-3-hydroxybenzisoxazol-O-(2-propionic acid, methyl ester)

A mixture of 3.30 grams (0.01 mole) of 5-(2-chloro-4-trifluoromethylphenoxy)-3-hydroxybenzisoxazole (prepared as described in Example I), 2.50 grams (0.015 mole) of methyl 2-bromopropionate, 50 milliliters of acetone and 1.52 grams (0.015 mole) of triethylamine was heated to reflux and maintained at reflux to about 48 hours. The progress of the reaction was monitored by HPLC and additional incremental amounts of triethylamine and methyl 2-bromopropionate being added over the course of the reflux period. The mixture was then cooled and solvent was evaporated at reduced pressure. Water and methylene chloride were added to the residue and after phase separation, the organic layer was washed twice with water. Evaporation of solvent at reduced pressure afforded 4.67 grams of oil which was purified by column chromatography and identified as the desired product, 5-(2-chloro-4-trifluoromethylphenoxy)-3-hydroxybenzisoxazol-O-(2-propionic acid, methyl ester), having a molecular weight of 415 as determined by mass spectrometry.

EXAMPLE III

Preparation of:
5-(2-chloro-4-trifluoromethylphenoxy)-3-hydroxybenzisoxazol-O-(acetic acid, methylthioester)

A mixture of 2.64 grams (0.008 mole) of 5-(2-chloro-4-trifluoromethylphenoxy)-3-hydroxybenzisoxazole (prepared as described in Example I), 1.60 grams (0.0128 mole) of S-methyl chlorothioacetate, 40 milliliters of acetonitrile, 2.02 grams (0.0146 mole) of potassium carbonate and 0.13 gram (0.0004 mole) of tetrabutyl ammonium bromide was heated, with stirring, to a temperature of 65°±5° C. and maintained thereat for about 36 hours, during which time were added an additional 0.13 gram of tetrabutyl ammonium bromide, 1.00 gram of potassium carbonate, and 0.82 gram of methyl chlorothioacetate, the progress of the reaction being monitored by HPLC. The mixture was then cooled and solvent was evaporated at reduced pressure. Water and methylene chloride were added to the residue and the organic phase was washed three times with water. Evaporation of solvent at reduced pressure afforded 3.07 grams of viscous, dark-red oil which was purified by column chromatography and identified by MS and NMR analyses as the desired product, 5-(2-chloro-4-trifluoromethylphenoxy)-3-hydroxybenzisoxazol-O-(acetic acid, methylthioester).

EXAMPLE IV

Preparation of:
5-(2-chloro-4-trifluoromethylphenoxy)-3-hydroxybenzisoxazole-O-(2-propionic acid, methylester), S-isomer A stirred mixture of 6.59 grams (0.02 mole) of 5-(2-chloro-4-trifluoromethylphenoxy)-3-hydroxybenzisoxazole (prepared as described in Example I), 48.3 grams of dimethyl formamide, 3.21 grams of methyl 2-chloropionate (R-isomer obtained from Rhone-Poulenc, Inc.) and 3.59 grams (0.026 mole) of potassium carbonate was heated to and maintained at about 40° C. by means of a Thermomatch, the progress of the reaction being monitored by HPLC. After about 23 hours an additional 1.0 gram each of potassium carbonate and methyl 2-chloropropionate R-isomer were added, heating was discontinued and the stirred mixture was allowed to cool to room temperature. Solvent was then evaporated at reduced pressure and the residue was dissolved in a mixture of methylene chloride and water. After phase separation, the organic layer was washed with water and solvent was evaporated at reduced pressure affording 8.53 grams of oil. The oil was passed through a silica gel-filled column and eluted with methylene chloride affording 5.98 grams of oil identified as the desired product, a solution of which in 25 milliliters of methylene chloride rotated a plane of polarized light +5°.

EXAMPLE V

Preparation of:
5-(2-chloro-4-trifluoromethylphenoxy)-3-hydroxybenzisoxazole-O-(2-propionic acid, ethylester), S-isomer A mixture of 1.98 grams (0.006 mole) of 5-(2-chloro-4-trifluoromethylphenoxy)-3-(hydroxybenzisoxazole (prepared as described in Example I), 30 milliliters of dimethyl formamide, 1.05 grams (0.0076 mole) of potassium carbonate and 1.04 grams (0.006 mole of ethyl 2-chloropropionate (R-isomer, Rhone-Poulenc, Inc. Lot No. 43-66-65, ($\alpha_D^{26}$+20.48°) was stirred at room temperature the progress of the reaction being monitored by HPLC. After about 23 hours stirring at room temperature, the mixture was heated to and maintained at about 50° C. for an additional 3½ hours. The mixture was then cooled and solvent was evaporated at reduced pressure. The residue was dissolved in a mixture of methylene chloride and water and after phase separation the organic phase was washed twice with water. Evaporation of solvent afforded 2.57 grams of oily residue. The residue was passed through a column packed with silica gel and eluted with methylne chloride, affording 2.09 grams of oil identified as the desired product.

The compounds prepared in the foregoing Examples I through V are represented by the following Formula VI:

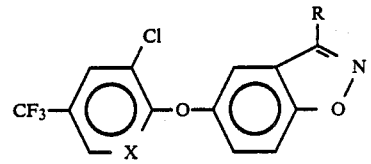

wherein X and R are as follows:

| Example | X  | R |
|---------|----|---|
| I       | CH | —OCH$_2$COOCH$_3$ |
| II      | CH | —OCH(CH$_3$)COOCH$_3$ |
| III     | CH | —OCH$_2$COSCH$_3$ |
| IV      | CH | —OC*H(CH$_3$)COOCH$_3$ (S—isomer) |
| V       | CH | —OC*H(CH$_3$)COOCH$_2$CH$_3$ (S—isomer) |

EXAMPLES VI through XXIII

Following the procedures described in the foregoing Examples, the following compounds of the above Formula VI were also prepared wherein X and R are as follows:

| Example | X  | R |
|---------|----|---|
| VI      | CH | —OCH$_2$CH=CHCOOCH$_3$ |
| VII     | CH | —OCH$_2$CH$_2$CH$_2$COOCH$_2$CH$_3$ |
| VIII    | CH | —OCH(CH$_3$)COOCH$_2$CH$_3$ |
| IX      | CH | —OCH(F)COOCH$_3$ |
| X       | CH | —OCH$_2$COOCH$_2$CH$_2$Cl |
| XI      | CH | —OC*H(CH$_3$)COOCH$_3$ (R—isomer) |
| XII     | CH | —OCH$_2$N$^\oplus$(CH$_3$)$_2$CH$_2$COOCH$_3$Br$^\ominus$ |
| XIII    | N  | —OCH(CH$_3$)COOCH$_3$ |
| XIV     | CH | —OCH$_2$COOH |
| XV      | CH | —OCH$_2$COON=C(CH$_3$)$_2$ |
| XVI     | CH | —OCH(CH$_3$)COOCH(CH$_3$)CH$_3$ |
| XVII    | CH | —OCH$_2$CON(CH$_3$)$_2$ |
| XVIII   | CH | —OCH$_2$COOCH$_2$CH$_2$N(CH$_3$)$_2$ |
| XIX     | CH | —OCH$_2$CONHCH$_3$ |
| XX      | CH | —OCH$_2$CONH$_2$ |
| XXI     | CH | —OCH$_2$CON(CH$_3$)OCH$_3$ |
| XXII    | CH | —OCH(OCH$_3$)COOCH$_3$ |
| XXIII   | CH | —OCH$_2$CONHOCH$_2$COOCH$_3$ |

Although the invention has been illustrated by the foregoing Examples with regard to the preparation of specific compounds within the scope of Formula I, it is to be understood that all of other compounds within the scope of Formula I may readily be prepared by those skilled in the art by varying the choice of starting materials and using the same or similar techniques.

Weed control in accordance with this invention is effected by applying to the soil before emergence of weeds therefrom or to the plant after an emergence from the soil, a herbicidally effective amount of a compound of this invention. It is, of course, to be understood that the term "a compound of this invention" also includes mixtures of such compounds.

The term "herbicidally effective amount" is that amount of a compound of this invention required to so injure or damage weeds such that the weeds are incapable of recovering following application while not causing substantial injury to valuable crops amongst which the weeds might be growing. The quantity of a compound of this invention applied in order to exhibit a satisfactory herbicidal effect may vary over a wide range and depends on a variety of factors, such as, for example, hardiness of a particular weed species, extent of weed infestation, climatic conditions, soil conditions, method of application, and the like. Of course, the efficacy of a particular compound against a particular weed species may readily be determined by routine laboratory or field testing in a manner well known to the art. It is expected that satisfactory postemergence weed control can be had at a rate of application in the range of 0.0001 to 10 pounds per acre, and typically in the range of 0.01 to 5.0 pounds per acre.

Of course, a compound of this invention can be formulated according to routine methods with any of several known and commonly used herbicidal diluents, adjuvants and carriers. The formulations can contain liquid carriers and adjuvants such as organic solvents, as well as emulsifiers, stabilizers, dispersants, suspending agents, spreaders, penetrants, wetting agents and the like. Typical carriers utilized in dry formulations include clay, talc, diatomaceous earth, silica and the like. Preferred formulations are those in the form of wettable powders, flowables, dispersible granulates or aqueous emulsifiable concentrates which can be diluted with water at the site of application. Also, dry formulations such as granules, dusts, and the like, may be used.

When desired, a compound of this invention can be applied in combination with other herbicidal agents in an effort to achieve even broader vegetative control. Typical herbicides which can be conveniently combined with Formula I compound include atrazine, hexazinone, metribuzin, ametryn, cyanazine, cyprazine, prometon, prometryn, propazine, simazine, terbutryn, propham, alachlor, acifluorfen, bentazon, metolachlor and N,N-dialkyl thiocarbamates such as EPTC, butylate or vernolate. These, as well as other herbicides described, for example, in the *Herbicide Handbook of the Weed Science Society of America* may be used in combination with a compound or compounds of the invention. Typically such formulations will contain from about 5 to 95 percent by weight of a compound of this invention.

The herbicidal formulations contemplated herein can be applied by any of several methods known to the art. Generally, the formulation will be applied as an aqueous spray. Such application can be carried out by conventional ground equipment, or if desired, the sprays can be aerially applied. Soil incorporation of such surface applied herbicides is accomplished by natural leaching, and is of course facilitated by natural rainfall and melting snow. If desired, however, the herbicides can be incorporated into the soil by conventional tillage means.

Compounds of this invention are effective for preemergence control and particularly for postemergence control of a wide variety of broadleaf and grassy weeds. Typical of the various species of vegetative growth that may be controlled, combated, or eliminated are, for example, annuals such as pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, kochia, medic, ragweed, hemp, nettle, spurrey, pondweed, carpetweed, morningglory, ducksalad, cheatgrass, fall panicum, jimsonweed, witchgrass, watergrass, wild turnip, and similar annual grasses and weeds. Biennials that may be controlled include wild barley, campion, burdock, bull thistle, roundleaved mallow, purple star thistle, and the like. Perennials such as quackgrass, Johnsongrass, Canada thistle, curley dock, field chickweed, dandelion, Russian knapweed aster, horsetail ironweed, seabania, cattail, wintercress, horsenettle, nutsedge, milkweed, sicklepod, and the like may also be controlled by application of the compounds of this invention.

For example, the compounds prepared in the Examples were tested for postemergence herbicidal efficacy, against a variety of broadleaf and grassy weed species, under controlled laboratory conditions of light, humidity and temperature. A solvent solution of each compound was applied to test flats containing the various weed species, and herbicidal efficacy was determined by visual inspection, periodically after application of the compounds. Herbicidal efficacy was determined on a Numerical Injury Rating (NIR) scale of from 0 (no injury) to 10 (all plants dead). A NIR rating of 7 to 9 indicates severe injury; a NIR rating of 4 to 6 indicates moderate injury, i.e., plant growth is reduced to the extent that normal growth would be expected only under ideal conditions; and a NIR rating of 1 to 3 indicates slight injury.

The following table gives the postemergence NIR for each of the compounds of Examples I to V against each of the broadleaf and grassy species at the indicated rate of application in pounds per acre. The NIR was determined three weeks after application. The broadleaf (BL) weeds used in the tests were coffeeweed (COFE), jimsonweed (JMWD), tall morningglory (MNGY), wild mustard (MSTD), teaweed (TEAW), velvetleaf (VTLF), sicklepod (SKPD) and lambsquarter (LMBQ). The grassy (GR) weeds used were barynyardgrass (BNGS), Johnsongrass (JNGS), wild oats (WOAT) and yellow foxtail (YLFX).

| | Postemergence NIR | | | | |
| --- | --- | --- | --- | --- | --- |
| | I | II | III | IV | V |
| Compound: | 0.5 | 1.0 | 1.0 | 0.1 | 0.2 |
| BL-Rate | | | | | |
| COFE | 9 | 10 | 9 | 10 | 8 |
| JMWD | 10 | 10 | 10 | 10 | 10 |
| MNGY | 10 | 10 | 10 | 7 | 10 |
| MSTD | 10 | 10 | 10 | — | — |
| TEAW | 8 | 10 | 7 | 9 | 10 |
| VTLF | 10 | 10 | 10 | 10 | 10 |
| SKPD | — | — | — | 5 | 10 |
| LMBQ | — | — | — | 10 | 10 |
| Average BL | 9.5 | 10 | 9.3 | 8.7 | 9.7 |
| GR-Rate | | | | | |
| BNGS | 4 | 8 | 6 | 9 | 9 |
| JNGS | 8 | 8 | 6 | 5 | 3 |
| WOAT | 2 | 5 | 1 | 5 | 2 |
| YLFX | 5 | 8 | 6 | 7 | 7 |
| Average GR | 4.7 | 7.2 | 4.7 | 6.5 | 5.2 |

Although the invention has been described in considerable detail by the foregoing, it is to be understood that many variations may be made therein by those skilled in the art without departing from the spirit and scope thereof as defined by the appended claims.

I claim:

1. A compound, including stereo isomers thereof, represented by the formula:

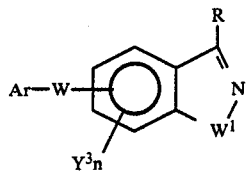

wherein Ar is

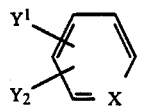

wherein:
W is oxygen;
$W^1$ is oxygen;
X is N or CY wherein Y is hydrogen, halogen, cyano, nitro or lower haloalkyl;
$Y^1$ and $Y^2$ are independently hydrogen, halogen, nitro, cyano or lower alkyl, haloalkyll, alkoxy, alkoxyalkyl or alkyl sulfonyl;
$Y^3$ is halogen, cyano, nitro or lower haloalkyl and n is 0, 1, 2 or 3;
R is

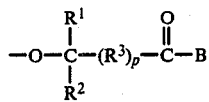

$R^1$ is hydrogen, halogen, nitro, cyano, or $C_1$ to $C_4$ alkyl, haloalkyl, cycloalkyl, alkoxy, alkoxydalkyl, carboxy or carboalkoxy or Ar, Ar-W, Ar-$R^4$ or Ar-$R^4$-W wherein $R^4$ is $C_1$ to $C_4$ alkyl;
$R^2$ is hydrogen, halogen or $C_1$ to $C_4$ alkyl;
$R^3$ is up to $C_3$ alkylene, alkenyl or alkynyl which may be mono or disubstituted by a member or members selected from $R^1$;
p is 0 or 1; and
B is $OR^5$ or $SR^5$ wherein:
$R^5$ is hydrogen, alkali metal, ammonium or substituted ammonium, or $C_1$ to $C_6$ alkyl, haloalkyl, oxoalkyl, hydroxyalkyl, thioalkyl, alkoxyalkyl, cycloalkyl, alkenyl, alkynyl or alkoxycarbonylalkyl or Ar or Ar-$R^8$ wherein $R^8$ is $C_1$ to $C_4$ alkyl, and including salts thereof.

2. A compound of claim 1 wherein $Y^1$ is a 2-halogen, $Y^2$ is a 4-lower haloalkyl, X is CY wherein Y is hydrogen or halogen, n is 0 and R is

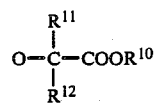

wherein $R^{11}$ is hydrogen or $C_1$ to $C_4$ alkyl; $R_{12}$ is hydrogen; and $R^{10}$ is $C_1$ to $C_4$ alkyl.

3. A compound of claim 2 wherein $Y^1$ is chlorine or fluorine, $Y^2$ is trifluoromethyl and Y is hydrogen, chlorine or fluorine.

4. A herbicidal formulation containing an inert carrier and a herbicidally effective amount of a compound or mixture of compounds defined by claim 1.

5. In a method of controlled weed growth wherein a herbicidally effective amount of herbicide is applied to the situs of the weeds, the improvement residing in using as the herbicide a compound or mixture of compounds defined by claim 1.

* * * * *